United States Patent [19]

Einhorn et al.

[11] Patent Number: 5,070,321

[45] Date of Patent: Dec. 3, 1991

[54] WARNING APPARATUS FOR A TRACHEOTOMY TUBE

[75] Inventors: Robert K. Einhorn, 138 Amith St., Apt. 1B; Istvan Szoke, 135 Willow St., Apt. 312, both of Brooklyn, N.Y. 11201

[73] Assignees: Robert K. Einhorn; Istvan Szoke; Ansel M. Schwartz

[21] Appl. No.: 539,694

[22] Filed: Jun. 18, 1990

[51] Int. Cl.$^5$ .............................................. G08B 21/00
[52] U.S. Cl. .................................. 340/608; 128/722; 128/724; 324/663
[58] Field of Search ........................ 340/608, 626, 573; 128/722, 724, 207.15; 324/663, 686, 690, 689; 73/204.11

[56] References Cited

U.S. PATENT DOCUMENTS

| | | | |
|---|---|---|---|
| 3,635,082 | 1/1972 | Prellwitz et al. | 324/690 X |
| 3,903,876 | 9/1975 | Harris | 340/608 X |
| 4,014,206 | 3/1977 | Taylor | 340/608 X |
| 4,182,344 | 4/1980 | Benson | 340/626 X |

OTHER PUBLICATIONS

"The Breath of Life... New Old... Radio Transmitter for Helmet Puts the X on Brain", Popular Mechanics, Jan. '71.

Primary Examiner—Donnie L. Crosland
Assistant Examiner—Jeffery A. Hofsass
Attorney, Agent, or Firm—Ansel M. Schwartz

[57] ABSTRACT

The present invention pertains to an apparatus for maintaining and monitoring a breathing passage in the trachea of a patient. The apparatus is comprised of a tracheotomy tube for fitting into the trachea. The apparatus is also comprised of means for warning when the tracheotomy tube become obstructed to air flow. In a preferred embodiment, the warning means includes a sensor in contact with the tracheotomy tube for sensing when the tracheotomy tube becomes obstructed. In a more preferred embodiment, the sensor includes at least one temperature sensor disposed such that the temperature of the air in the tracheotomy tube is sensed and produces the temperature sensor signal corresponding to the air temperature in the tracheotomy tube. The temperature sensor is in electrical connection with an alarm which indicates when the tube is obstructed. In another embodiment, the sensor includes a capacitor disposed in the tracheotomy tube such that the capacitance of the capacitor corresponds to the percent occlusion of the tube when obstructed.

2 Claims, 4 Drawing Sheets

WARNING APPARATUS FOR A TRACHEOTOMY TUBE

FIELD OF THE INVENTION

The present invention is related to tracheotomy tubes. More specifically, the present invention relates to tracheotomy tubes which provide a warning when the tube becomes obstructed.

BACKGROUND OF THE INVENTION

Today, tracheotomy is one of the more commonly performed procedures in otolaryngology and head and neck surgery.

Currently, a tracheotomy is performed for a variety of indications. The most common of these is airway obstruction, which can be either acute or chronic. Acute airway obstruction may be due to an infectious process, or any deep neck space infection.

Chronic airway obstruction is usually due to the presence of a mass, sometimes benign but most often malignant.

Tracheotomy may be done either at a patient's bedside, such as in an intensive care setting, or in the operating room. A midline skin incision is made from cricoid cartilage almost down to the jugulum. The trachea is then entered sharply, usually at the second or third ring. The orotracheal tube (if present) is withdrawn, and the airway is secured with the tracheotomy tube.

There are typically three parts to a traditional tracheotomy tube: an outer tube, an inner tube, and a stylet or obturator. A stylet or obturator is used to introduce the tube into the trachea. The stylet fills the end of the outer tube and provides a tapered point so that the advancing end does not tear tissue. Once the tube is in place, the stylet is withdrawn immediately, because while it is in place, there is no airway. The inner cannula is then inserted and locked in place. Gauze tapes previously attached to the outer tube are tied around the neck.

After the operation, the outer tube stays in the trachea until the surgeon believes it is safe to remove it for cleansing and inspection of the wound. Ordinarily, the nurse does not remove the outer tube unless specifically instructed by the physician because there is sometimes difficulty in replacing it. The mistake is to insert the tube into the soft tissue of the neck other than into the lumen of the trachea.

The inner tube is the province of the nurse. This tube fits the inside of the outer tube snugly, yet loosely enough that it can be removed by light finger traction.

In the immediate postoperative period, the inner tube should be removed, inspected and cleaned every two hours. If it is not done, small amounts of dried blood may cause difficulty in removing the cannula. It is by cleansing the inner tube that the airway is maintained. Cleaning is needed more often in a patient whose chest is filled with secretion than in a patient with laryngeal obstruction but no excessive secretions.

In a patient whose chest is filled with secretions, suctioning must be done frequently—as often as every five minutes. In other patients, suctioning every two or three hours or even once or twice a day may be all that is necessary. In suctioning, the aim is to aspirate all secretions that have accumulated in the tracheobronchial tree since the last suctioning and which the patient is unable to cough up himself.

Patients may develop obstructive plugs of dried mucus in the trachea that actually endanger his airway unless the tracheotomy tube is removed and the plug pulled out.

If the tube is coughed out, it is usually because the ties were not sufficiently tight or because the tube was too short. This can amount to an emergency if it occurs in the first few hours after tracheotomy, because a sufficient tract has not yet been formed between skin and trachea to sustain breathing. The tube must be reinserted at once.

To date, there are no devices to monitor the patency of tracheotomy tube. The present invention alerts the hospital staff to a clogged or dislodged tube.

SUMMARY OF THE INVENTION

The present invention pertains to an apparatus for maintaining a breathing passage in the trachea of a patient. The apparatus is comprised of a tracheotomy tube for fitting into the trachea. The apparatus is also comprised of means for warning when the tracheotomy tube becomes obstructed to air flow. In a preferred embodiment, the warning means includes a sensor in contact with the tracheotomy tube for sensing when the tracheotomy tube becomes obstructed. In a more preferred embodiment, the sensor includes at least one temperature sensor disposed such that the temperature of the air in the tracheotomy tube is sensed and produces the temperature sensor signal corresponding to the air temperature in the tracheotomy tube. The temperature sensor is in electrical connection with an alarm which indicates when the tube is obstructed. In another embodiment, the sensor includes a capacitor disposed in the tracheotomy tube such that the capacitance of the capacitor corresponds to the percent occlusion of the tube by the obstruction.

BRIEF DESCRIPTION OF THE DRAWINGS

In the accompanying drawings, the preferred embodiments of the invention and preferred methods of practicing the invention are illustrated in which.

DESCRIPTION OF THE PREFERRED EMBODIMENT

Figure 1:
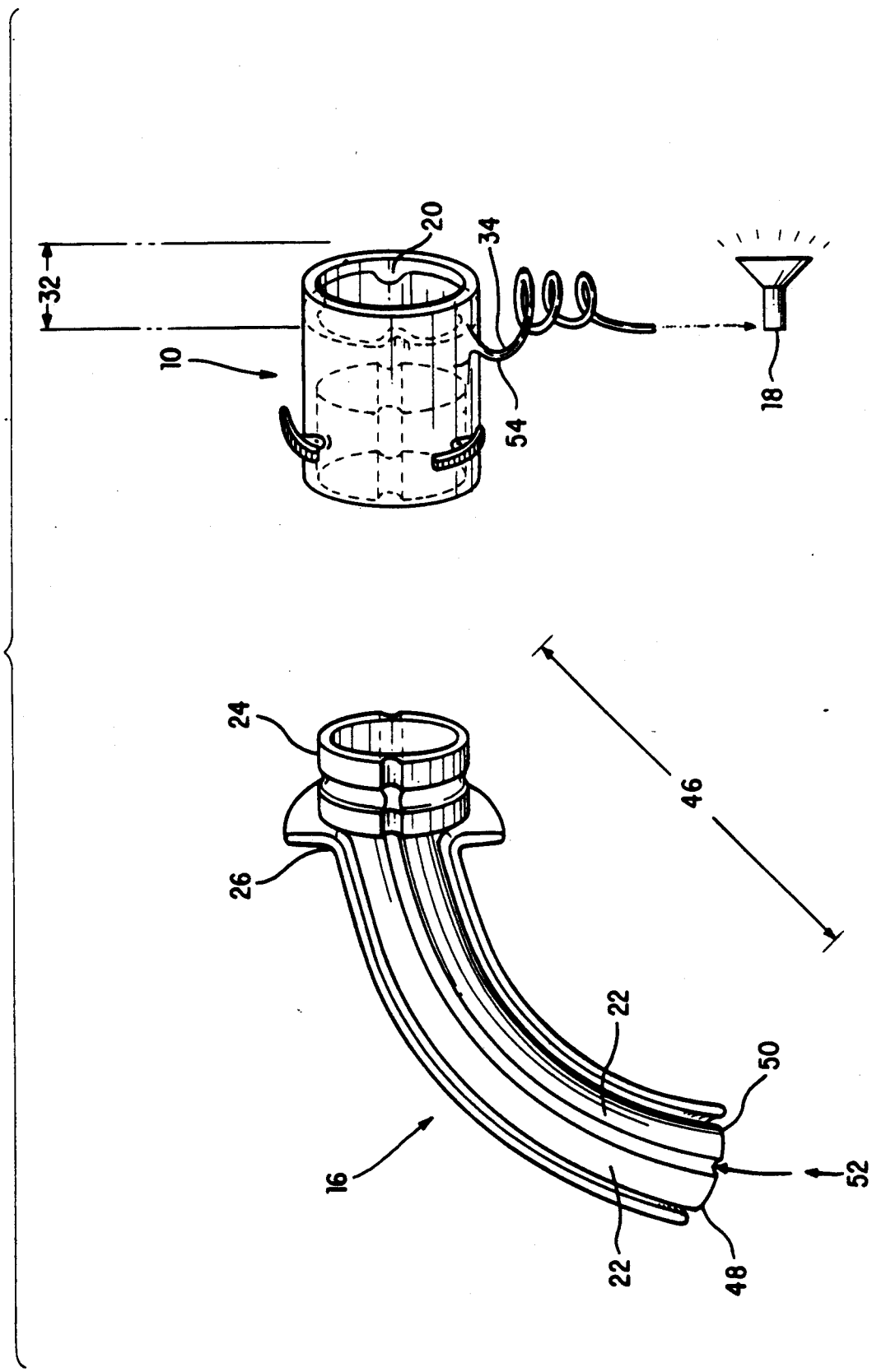
FIG. 1 is a schematic representation of the present invention.
Figure 2:
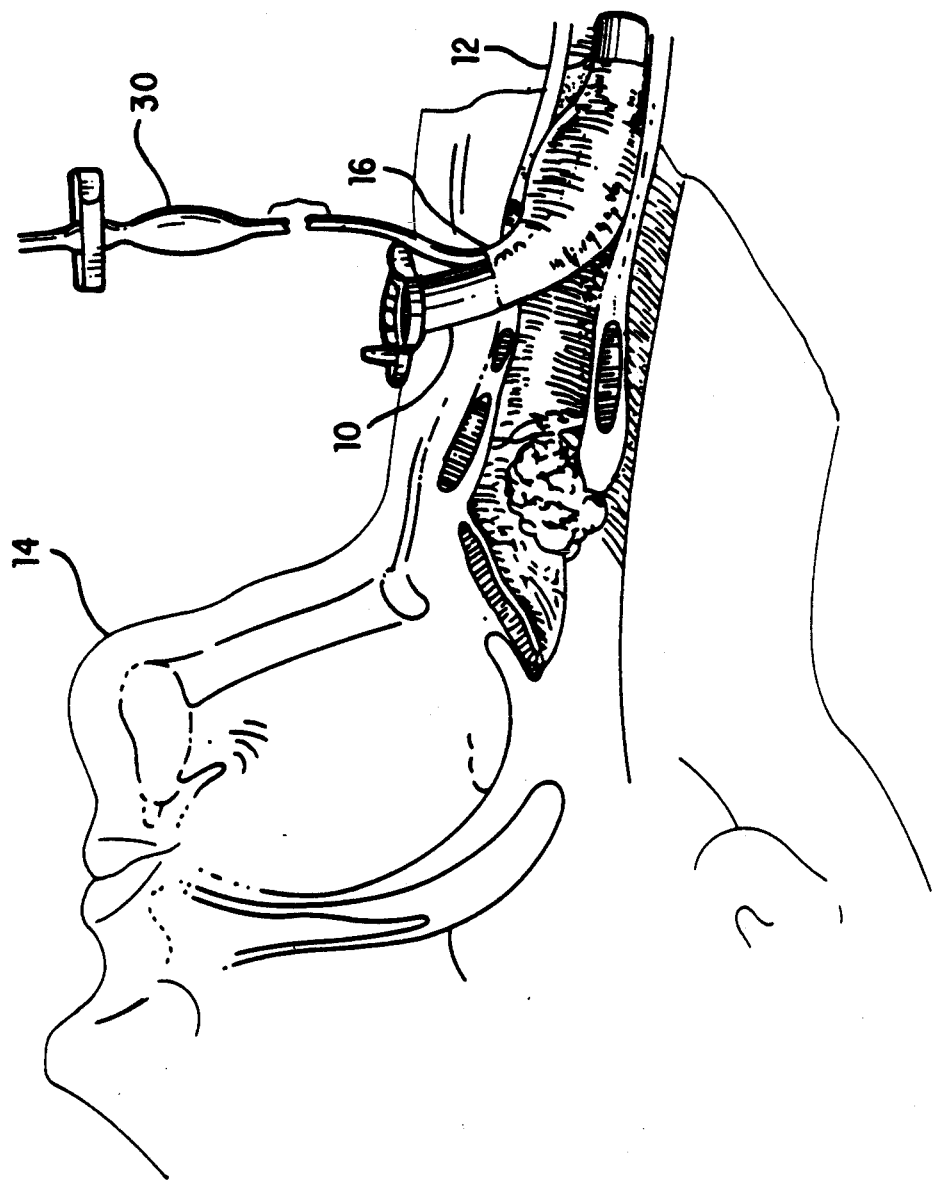
FIG. 2 is a schematic representation of the invention in a patient.
Figure 3:
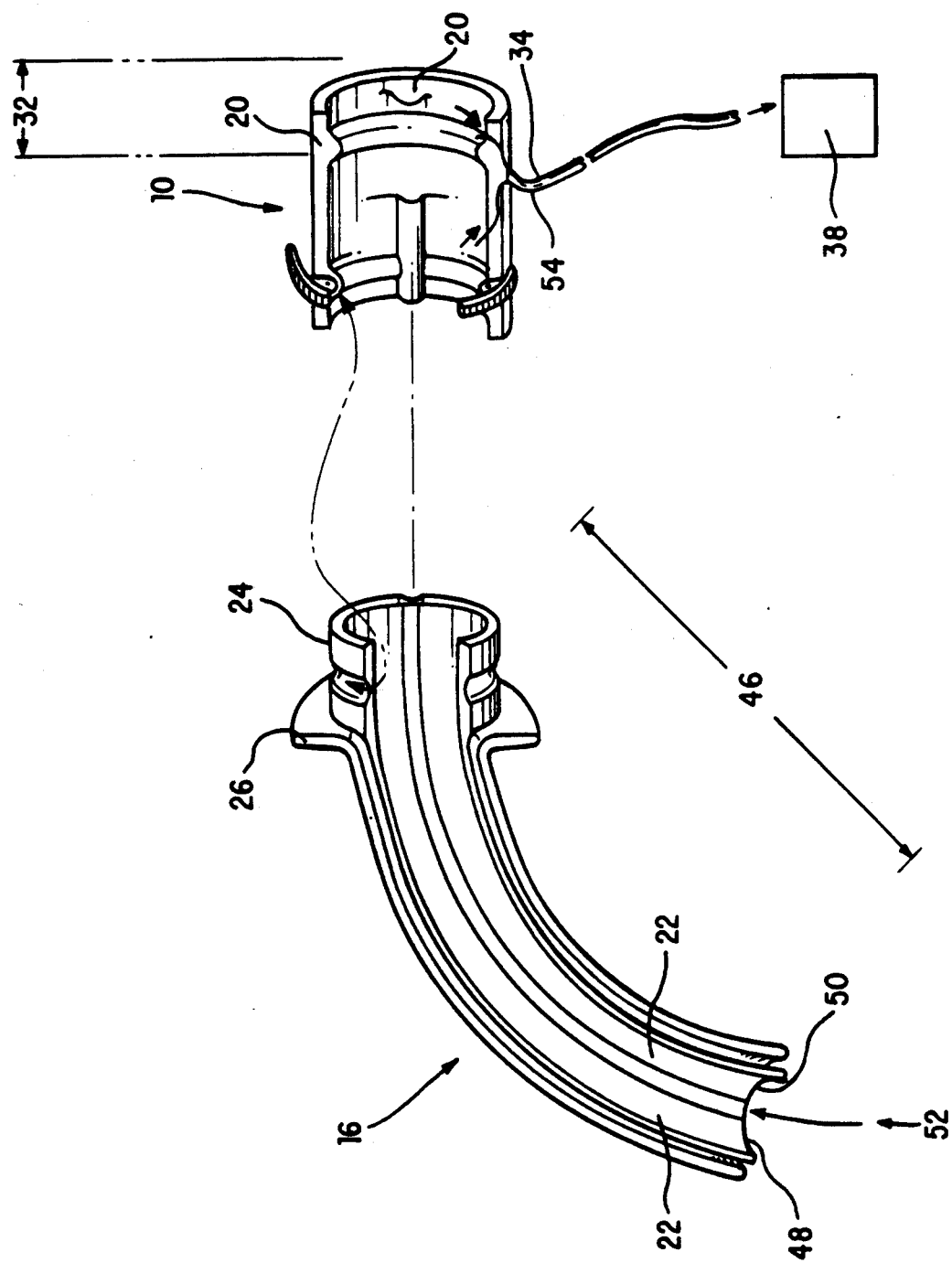
FIG. 3 is a cross sectional view of the invention.
Figure 4:
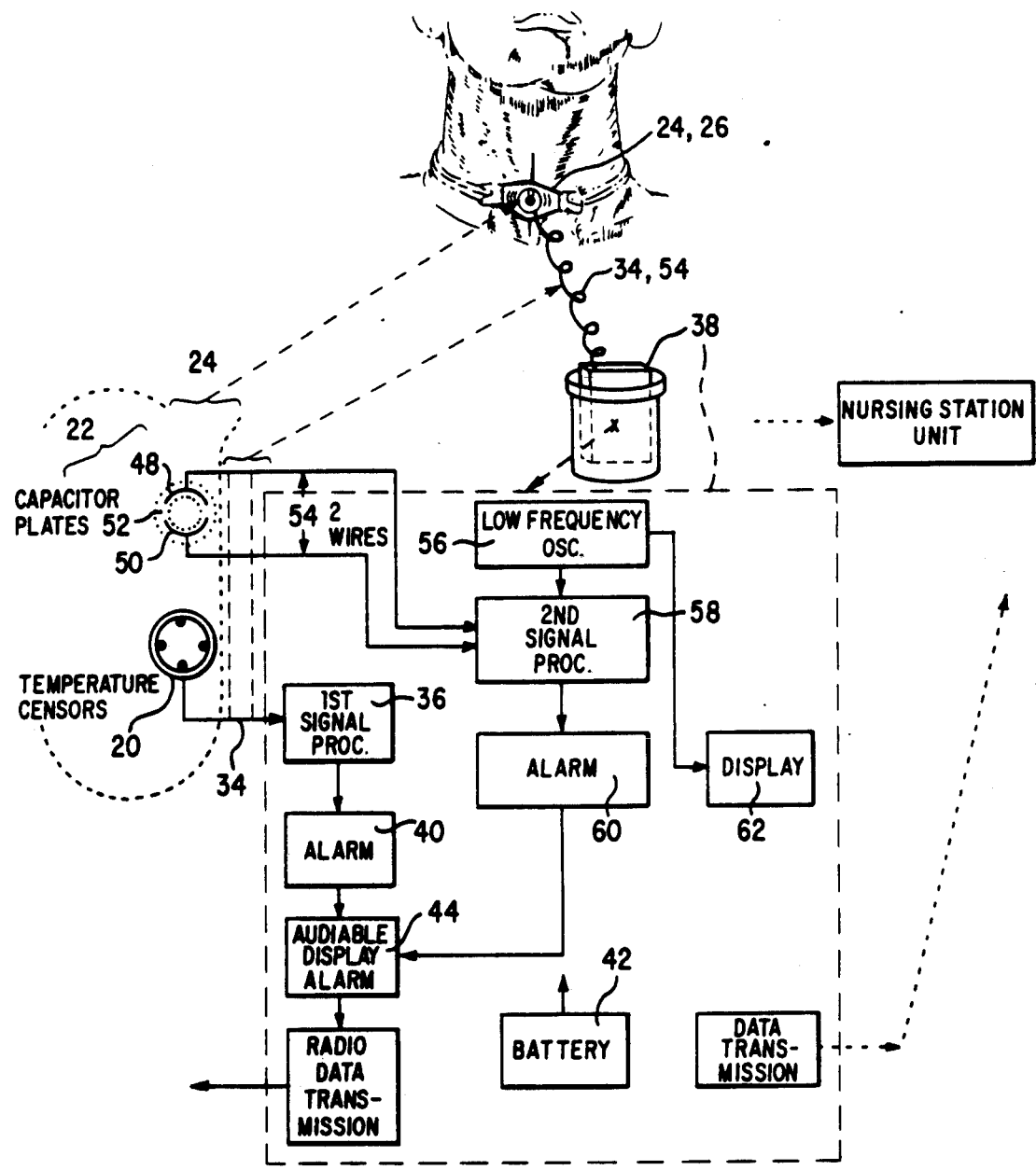
FIG. 4 is a block diagram of the invention.

Referring to the drawings wherein like reference numerals refer to similar or identical parts throughout the several views, and more specifically to FIG. 1 thereof, there is shown an apparatus 10 for maintaining a breathing passage in the trachea 12 of a patient 14. The apparatus 10 is comprised of a tracheotomy tube 16 for fitting into the trachea 12. The apparatus 10 is also comprised of means for warning when the tracheotomy tube 16 becomes obstructed to air flow. Preferably, the warning means includes a sensor in contact with the tracheotomy tube 16 for sensing when the tracheotomy tube 16 becomes obstructed. Both apparatuses include an alarm means 18 in communication with the sensor and which indicates when the tube 16 is obstructed.

In a first embodiment, the sensor includes at least one temperature sensor 20 disposed such that the temperature of the air in the tracheotomy tube 16 is sensed and produces a temperature sensor signal corresponding to the air temperature in the tracheotomy tube 16. The temperature sensor 20 is in electrical connection with the alarm means 18. In a second embodiment, the sensor includes a capacitor 22 disposed in the tracheotomy tube 16 such that the capacitance of the capacitor 22 corresponds to the percent occlusion of the tube 16 by the obstruction.

Preferably, the apparatus 10 includes an inner cannula 24 with the capacitor 22 disposed therein such that the capacitance of the capacitor 22 corresponds to the percent occlusion of the inner cannula 24 by an obstruction therein. The alarm means 18 is electrically connected to the capacitor 22 to indicate when the inner cannula 24 is obstructed.

In the operation of the preferred embodiment, an outer cannula 26 with an obturator (not shown) disposed therein is inserted into the trachea 12 of the patient 14. The bladder 30 not present in all tubes positioned about the outer cannula 26 of the trachea tube 16 is expanded to the proper position to anchor the tube 16 in the trachea 12 of the patient 14.

The obturator is then removed and the inner cannula 24 is inserted into the outer cannula 26. Temperature sensors 20 disposed in the end 32 of the inner cannula 24 which extends out of patient 14 senses the temperature of the air passing in and out of the patient through the trachea tube 16. The temperature of the air which is exhaled is several degrees warmer than the temperature of the air inhaled in a typical hospital environment.

A first lead 34 connected to the temperature sensors 20 is also connected to the first signal processing circuit 36 disposed in a housing 38 fitted onto the patient 14, for instance in a pocket of his or her pajamas. The first signal processing circuit 36 provides a processed signal to a first alarm circuit 40. The first alarm circuit 40, which is powered by a battery 42 provides an alarm signal to an audio visual alarm 44, when the temperature sensors 20 do not detect a change in air temperature over a preset time interval period. A failure in the air temperature change in time set can be due to dislodging of the inner cannula 24 or cessation of breathing patterns due to some failure in the physiology of the patient, or the trachea tube 16 coming out of the patient 14.

In the portion 46 of the inner cannula 24 that is disposed in the patient 14 there is a first plate 48 and a second plate 50 with insulation 52 disposed therebetween, all of which are built into the inner cannula 24. The first plate 48 and second plate 50 together form a capacitor 22. Second leads 54 connected to the first plate 48 and second plate 50 extend out to a low frequency oscillator 56 in the housing 38. A signal from the oscillator 56 received by a second signal processing circuit 58 which processes the signal and provides it to a second alarm circuit 60. The alarm circuit 60 provides that signal to a display 62 which displays the percent occlusion of the inner cannula 24. If the percent occlusion is over a predetermined amount, the audio visual alarm 44 is activated. The display 62, second alarm circuit 60, second signal processing circuit 58 and low frequency oscillator 56 are also powered by the batteries 42.

If any type of discharge fills the inner cannula 24, this causes a change in the capacitance of the capacitor 22 due to change in the dielectric constant between the first plate 48 and second plate 50 in the capacitor 22. Accordingly, the capacitance of the capacitor 22 corresponds to the percentage occlusion in the inner cannula 24.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for maintaining a breathing passage in the trachea of a patient comprising:

a tracheotomy tube for fitting into the trachea;

means for warning when the tracheotomy tube becomes obstructed to air flow, said warning means includes a sensor in contact with the tracheotomy tube for sensing when the tracheotomy tube becomes obstructed, said sensor includes at least one temperature sensor disposed such that the temperature of the air in the tracheotomy tube is sensed and produces a temperature sensor signal corresponding to the air temperature in the tracheotomy tube, said sensor also includes a capacitor disposed in the tracheotomy tube such that the capacitance of the capacitor corresponds to the percent occlusion of the tube by an obstruction; and an alarm means in communication with the temperature sensor and the capacitor which indicates when the tube is obstructed.

2. A warning apparatus for a tracheotomy tube comprising:

an inner cannula with a capacitor disposed therein such that the capacitance of the capacitor corresponds to the percent occlusion of the inner cannula by an obstruction therein, and an alarm means electrically connected to the capacitor to indicate when the inner cannula is obstructed.

* * * * *